(12) United States Patent
Platt et al.

(10) Patent No.: US 9,289,573 B2
(45) Date of Patent: Mar. 22, 2016

(54) VENTILATOR PRESSURE OSCILLATION FILTER

(71) Applicant: COVIDIEN LP, Boulder, CO (US)

(72) Inventors: Clayton R. Platt, Lake Forest, CA (US); Fang Zheng, Irvine, CA (US); Rick Crawford, Yucaipa, CA (US)

(73) Assignee: Covidien LP, Mansfield, MA (US)

( * ) Notice: Subject to any disclaimer, the term of this patent is extended or adjusted under 35 U.S.C. 154(b) by 440 days.

(21) Appl. No.: 13/730,513

(22) Filed: Dec. 28, 2012

(65) Prior Publication Data
US 2014/0182590 A1    Jul. 3, 2014

(51) Int. Cl.
| A61M 16/20 | (2006.01) |
|---|---|
| A61M 16/10 | (2006.01) |
| A61M 16/00 | (2006.01) |
| A61M 16/04 | (2006.01) |
| A61M 16/06 | (2006.01) |
| A61M 16/08 | (2006.01) |

(52) U.S. Cl.
CPC .......... *A61M 16/201* (2014.02); *A61M 16/105* (2013.01); *A61M 16/20* (2013.01); *A61M 16/202* (2014.02); *A61M 16/0006* (2014.02); *A61M 16/0051* (2013.01); *A61M 16/0057* (2013.01); *A61M 16/0096* (2013.01); *A61M 16/04* (2013.01); *A61M 16/06* (2013.01); *A61M 16/0816* (2013.01); *A61M 16/0875* (2013.01); *A61M 2205/502* (2013.01); *A61M 2205/8206* (2013.01)

(58) Field of Classification Search
CPC ... A61M 16/00; A61M 16/20; A61M 16/201; A61M 16/202; A61M 16/203; A61M 16/204; A61M 16/205; A61M 16/206; A61M 16/207; A61M 16/209; A61M 16/0096; A62B 9/02; A62B 9/022; Y10T 137/87378; Y10T 137/87394; Y10T 137/87507; Y10T 137/87555; Y10T 137/87563
USPC .............................. 128/205.24; 137/602, 605
See application file for complete search history.

(56) References Cited

U.S. PATENT DOCUMENTS

| 376,819 | A | 1/1888 | Glew |
|---|---|---|---|
| 883,987 | A | 4/1908 | Teter |
| 1,686,504 | A | 10/1928 | Dodge et al. |
| 1,858,400 | A | 5/1932 | Koehler |
| 3,066,674 | A | 12/1962 | Capra |

(Continued)

OTHER PUBLICATIONS

PCT International Search Report and Written Opinion in International Application PCT/US2013/077679, mailed Apr. 3, 2014, 7 pgs.

(Continued)

*Primary Examiner* — Justine Yu
*Assistant Examiner* — Colin W Stuart

(57) ABSTRACT

A ventilation air pressure oscillation mitigation device for a ventilator includes a housing defining an inlet and an outlet. The device includes a valve seat defining a primary opening and a plurality of secondary openings. A valve body is selectively positionable in a first position and a second position within the device. In the first position, substantially all of a first flow of ventilation air from the inlet to the outlet passes through the primary opening. When the valve body is in the second position, all of a second flow of ventilation air from the inlet to the outlet passes through the plurality of secondary openings. An actuator controls a position of the valve body.

8 Claims, 9 Drawing Sheets

(56) References Cited

U.S. PATENT DOCUMENTS

| | | |
|---|---|---|
| 3,415,245 A | 12/1968 | Yamamoto et al. |
| 3,918,447 A | 11/1975 | Inkster et al. |
| 3,981,636 A | 9/1976 | Aoki et al. |
| 4,055,173 A | 10/1977 | Knab |
| 4,127,130 A | 11/1978 | Naysmith |
| 4,211,239 A | 7/1980 | Raemer et al. |
| 4,259,951 A | 4/1981 | Chernack et al. |
| 4,269,196 A | 5/1981 | Toms et al. |
| 4,381,267 A | 4/1983 | Jackson |
| 4,449,537 A | 5/1984 | Pross et al. |
| 4,714,078 A | 12/1987 | Paluch |
| 4,752,089 A | 6/1988 | Carter |
| 4,799,263 A | 1/1989 | Banziger et al. |
| 4,921,642 A | 5/1990 | LaTorraca |
| 4,954,799 A | 9/1990 | Kumar |
| 5,036,843 A * | 8/1991 | Schreurs ............... 128/205.24 |
| 5,057,822 A | 10/1991 | Hoffman |
| 5,072,737 A | 12/1991 | Goulding |
| 5,150,291 A | 9/1992 | Cummings et al. |
| 5,161,525 A | 11/1992 | Kimm et al. |
| 5,237,987 A | 8/1993 | Anderson et al. |
| 5,271,389 A | 12/1993 | Isaza et al. |
| 5,279,549 A | 1/1994 | Ranford |
| 5,299,568 A | 4/1994 | Forare et al. |
| 5,301,921 A | 4/1994 | Kumar |
| 5,309,922 A | 5/1994 | Schechter et al. |
| 5,319,540 A | 6/1994 | Isaza et al. |
| 5,323,772 A | 6/1994 | Linden et al. |
| 5,325,861 A | 7/1994 | Goulding |
| 5,333,606 A | 8/1994 | Schneider et al. |
| 5,339,807 A | 8/1994 | Carter |
| 5,343,857 A | 9/1994 | Schneider et al. |
| 5,351,522 A | 10/1994 | Lura |
| 5,357,946 A | 10/1994 | Kee et al. |
| 5,368,019 A | 11/1994 | LaTorraca |
| 5,383,449 A | 1/1995 | Forare et al. |
| 5,385,142 A | 1/1995 | Brady et al. |
| 5,390,666 A | 2/1995 | Kimm et al. |
| 5,401,135 A | 3/1995 | Stoen et al. |
| 5,402,796 A | 4/1995 | Packer et al. |
| 5,407,174 A | 4/1995 | Kumar |
| 5,413,110 A | 5/1995 | Cummings et al. |
| 5,438,980 A | 8/1995 | Phillips |
| 5,443,075 A | 8/1995 | Holscher |
| 5,513,631 A | 5/1996 | McWilliams |
| 5,517,983 A | 5/1996 | Deighan et al. |
| 5,520,071 A | 5/1996 | Jones |
| 5,524,615 A | 6/1996 | Power |
| 5,531,221 A | 7/1996 | Power et al. |
| 5,542,415 A | 8/1996 | Brody |
| 5,544,674 A | 8/1996 | Kelly |
| 5,549,106 A | 8/1996 | Gruenke et al. |
| 5,596,984 A | 1/1997 | O'Mahony et al. |
| 5,630,411 A | 5/1997 | Holscher |
| 5,632,270 A | 5/1997 | O'Mahony et al. |
| 5,645,048 A | 7/1997 | Brodsky et al. |
| 5,645,071 A | 7/1997 | Harnoncourt et al. |
| 5,655,520 A | 8/1997 | Howe et al. |
| 5,660,171 A | 8/1997 | Kimm et al. |
| 5,664,560 A | 9/1997 | Merrick et al. |
| 5,664,562 A | 9/1997 | Bourdon |
| 5,671,767 A | 9/1997 | Kelly |
| 5,672,041 A | 9/1997 | Ringdahl et al. |
| 5,673,689 A | 10/1997 | Power |
| 5,715,812 A | 2/1998 | Deighan et al. |
| 5,762,480 A | 6/1998 | Adahan |
| 5,771,884 A | 6/1998 | Yarnall et al. |
| 5,791,339 A | 8/1998 | Winter |
| 5,794,986 A | 8/1998 | Gansel et al. |
| 5,813,399 A | 9/1998 | Isaza et al. |
| 5,826,575 A | 10/1998 | Lall |
| 5,829,441 A | 11/1998 | Kidd et al. |
| 5,864,938 A | 2/1999 | Gansel et al. |
| 5,865,168 A | 2/1999 | Isaza |
| 5,881,717 A | 3/1999 | Isaza |
| 5,881,723 A | 3/1999 | Wallace et al. |
| 5,884,623 A | 3/1999 | Winter |
| 5,909,731 A | 6/1999 | O'Mahony et al. |
| 5,915,379 A | 6/1999 | Wallace et al. |
| 5,915,380 A | 6/1999 | Wallace et al. |
| 5,915,382 A | 6/1999 | Power |
| 5,918,597 A | 7/1999 | Jones et al. |
| 5,921,238 A | 7/1999 | Bourdon |
| 5,934,274 A | 8/1999 | Merrick et al. |
| 6,024,089 A | 2/2000 | Wallace et al. |
| 6,041,780 A | 3/2000 | Richard et al. |
| 6,047,860 A | 4/2000 | Sanders |
| 6,076,523 A | 6/2000 | Jones et al. |
| 6,085,746 A | 7/2000 | Fox |
| 6,089,230 A | 7/2000 | Barker et al. |
| 6,116,240 A | 9/2000 | Merrick et al. |
| 6,116,464 A | 9/2000 | Sanders |
| 6,123,073 A | 9/2000 | Schlawin et al. |
| 6,135,106 A | 10/2000 | Dirks et al. |
| 6,142,150 A | 11/2000 | O'Mahoney et al. |
| 6,161,539 A | 12/2000 | Winter |
| 6,168,568 B1 | 1/2001 | Gavriely |
| 6,216,691 B1 | 4/2001 | Kenyon et al. |
| 6,220,245 B1 | 4/2001 | Takabayashi et al. |
| 6,260,549 B1 | 7/2001 | Sosiak |
| 6,269,812 B1 | 8/2001 | Wallace et al. |
| 6,273,444 B1 | 8/2001 | Power |
| 6,279,574 B1 | 8/2001 | Richardson et al. |
| 6,283,119 B1 | 9/2001 | Bourdon |
| 6,305,373 B1 | 10/2001 | Wallace et al. |
| 6,318,361 B1 | 11/2001 | Sosiak |
| 6,321,748 B1 | 11/2001 | O'Mahoney |
| 6,325,785 B1 | 12/2001 | Babkes et al. |
| 6,357,438 B1 | 3/2002 | Hansen |
| 6,360,745 B1 | 3/2002 | Wallace et al. |
| 6,369,838 B1 | 4/2002 | Wallace et al. |
| 6,412,483 B1 | 7/2002 | Jones et al. |
| 6,425,392 B1 | 7/2002 | Sosiak |
| 6,439,229 B1 | 8/2002 | Du et al. |
| 6,467,478 B1 | 10/2002 | Merrick et al. |
| 6,516,800 B1 | 2/2003 | Bowden |
| 6,546,930 B1 | 4/2003 | Emerson et al. |
| 6,553,991 B1 | 4/2003 | Isaza |
| 6,557,553 B1 | 5/2003 | Borrello |
| 6,571,795 B2 | 6/2003 | Bourdon |
| 6,615,831 B1 | 9/2003 | Tuitt et al. |
| 6,622,726 B1 | 9/2003 | Du |
| 6,644,310 B1 | 11/2003 | Delache et al. |
| 6,644,311 B1 | 11/2003 | Truitt et al. |
| 6,668,824 B1 | 12/2003 | Isaza et al. |
| 6,675,801 B2 | 1/2004 | Wallace et al. |
| 6,691,707 B1 | 2/2004 | Gunaratnam et al. |
| 6,718,974 B1 | 4/2004 | Moberg |
| 6,725,447 B1 | 4/2004 | Gilman et al. |
| 6,739,337 B2 | 5/2004 | Isaza |
| 6,761,167 B1 | 7/2004 | Nadjafizadeh et al. |
| 6,761,168 B1 | 7/2004 | Nadjafizadeh et al. |
| 6,814,074 B1 | 11/2004 | Nadjafizadeh et al. |
| 6,866,040 B1 | 3/2005 | Bourdon |
| 6,949,133 B2 | 9/2005 | McCombs et al. |
| 6,960,854 B2 | 11/2005 | Nadjafizadeh et al. |
| 7,036,504 B2 | 5/2006 | Wallace et al. |
| 7,077,131 B2 | 7/2006 | Hansen |
| RE39,225 E | 8/2006 | Isaza et al. |
| 7,117,438 B2 | 10/2006 | Wallace et al. |
| 7,270,126 B2 | 9/2007 | Wallace et al. |
| 7,341,059 B2 | 3/2008 | Moody et al. |
| 7,369,757 B2 | 5/2008 | Farbarik |
| 7,370,650 B2 | 5/2008 | Nadjafizadeh et al. |
| 7,428,902 B2 | 9/2008 | Du et al. |
| 7,460,959 B2 | 12/2008 | Jafari |
| 7,487,773 B2 | 2/2009 | Li |
| 7,490,604 B2 | 2/2009 | McGee |
| 7,654,802 B2 | 2/2010 | Crawford, Jr. et al. |
| 7,694,677 B2 | 4/2010 | Tang |
| 7,717,113 B2 | 5/2010 | Andrieux |
| D618,356 S | 6/2010 | Ross |
| 7,784,461 B2 | 8/2010 | Figueiredo et al. |
| 7,823,588 B2 | 11/2010 | Hansen |

(56) References Cited

U.S. PATENT DOCUMENTS

| | | |
|---|---|---|
| 7,855,716 B2 | 12/2010 | McCreary et al. |
| D632,796 S | 2/2011 | Ross et al. |
| D632,797 S | 2/2011 | Ross et al. |
| 7,891,354 B2 | 2/2011 | Farbarik |
| 7,893,560 B2 | 2/2011 | Carter |
| 7,896,808 B1 | 3/2011 | Koh |
| D638,852 S | 5/2011 | Skidmore et al. |
| 7,975,688 B1 | 7/2011 | Truitt |
| 7,984,714 B2 | 7/2011 | Hausmann et al. |
| D643,535 S | 8/2011 | Ross et al. |
| 7,992,557 B2 | 8/2011 | Nadjafizadeh et al. |
| 8,001,967 B2 | 8/2011 | Wallace et al. |
| D645,158 S | 9/2011 | Sanchez et al. |
| 8,021,310 B2 | 9/2011 | Sanborn et al. |
| D649,157 S | 11/2011 | Skidmore et al. |
| D652,521 S | 1/2012 | Ross et al. |
| D652,936 S | 1/2012 | Ross et al. |
| D653,749 S | 2/2012 | Winter et al. |
| 8,113,062 B2 | 2/2012 | Graboi et al. |
| D655,405 S | 3/2012 | Winter et al. |
| D655,809 S | 3/2012 | Winter et al. |
| D656,237 S | 3/2012 | Sanchez et al. |
| 8,181,648 B2 | 5/2012 | Perine et al. |
| 8,210,173 B2 | 7/2012 | Vandine |
| 8,210,174 B2 | 7/2012 | Farbarik |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 8,457,706 B2 | 6/2013 | Baker, Jr. |
| 8,792,949 B2 | 7/2014 | Baker, Jr. |
| 2002/0014241 A1 | 2/2002 | Gradon et al. |
| 2002/0046753 A1 | 4/2002 | Lamb |
| 2002/0073994 A1 | 6/2002 | Patel |
| 2002/0078958 A1 | 6/2002 | Stenzler |
| 2002/0097881 A1 | 7/2002 | Flugger |
| 2002/0134378 A1 | 9/2002 | Finnegan et al. |
| 2003/0079751 A1 | 5/2003 | Kwok |
| 2003/0172931 A1 | 9/2003 | Kerechanin et al. |
| 2004/0025881 A1 | 2/2004 | Gunaratnam et al. |
| 2004/0035422 A1 | 2/2004 | Truitt et al. |
| 2004/0040559 A1 | 3/2004 | Moody et al. |
| 2004/0065327 A1 | 4/2004 | Gradon et al. |
| 2004/0186386 A1 | 9/2004 | Kolluri et al. |
| 2004/0221845 A1 | 11/2004 | Pranger et al. |
| 2005/0000519 A1 | 1/2005 | Friberg et al. |
| 2005/0039748 A1 | 2/2005 | Andrieux |
| 2005/0045175 A1 | 3/2005 | McCawley et al. |
| 2005/0139212 A1 | 6/2005 | Bourdon |
| 2005/0166921 A1 | 8/2005 | DeVries et al. |
| 2005/0178386 A1 | 8/2005 | Moody et al. |
| 2005/0222513 A1 | 10/2005 | Hadley et al. |
| 2005/0229929 A1 | 10/2005 | Ivri |
| 2005/0241642 A1 | 11/2005 | Krzysztofik |
| 2006/0037618 A1 | 2/2006 | Halbert |
| 2006/0124130 A1 | 6/2006 | Bonassa |
| 2006/0144396 A1 | 7/2006 | DeVries et al. |
| 2006/0144405 A1 | 7/2006 | Gunaratnam et al. |
| 2006/0213518 A1 | 9/2006 | DeVries et al. |
| 2006/0249158 A1 | 11/2006 | Dhuper et al. |
| 2006/0253038 A1 | 11/2006 | Kuck et al. |
| 2007/0000490 A1 | 1/2007 | DeVries et al. |
| 2007/0004988 A1 | 1/2007 | Wu et al. |
| 2007/0017515 A1 | 1/2007 | Wallace et al. |
| 2007/0048159 A1 | 3/2007 | DiMatteo et al. |
| 2007/0068518 A1 | 3/2007 | Urias et al. |
| 2007/0077200 A1 | 4/2007 | Baker |
| 2007/0157930 A1 | 7/2007 | Soliman et al. |
| 2007/0169776 A1 | 7/2007 | Kepler et al. |
| 2007/0169781 A1 | 7/2007 | Tang |
| 2007/0193579 A1 | 8/2007 | Duquette et al. |
| 2007/0193580 A1 | 8/2007 | Feldhahn et al. |
| 2007/0208267 A1 | 9/2007 | Schmid et al. |
| 2007/0227537 A1 | 10/2007 | Bemister et al. |
| 2007/0240709 A1 | 10/2007 | Woolley et al. |
| 2007/0272241 A1 | 11/2007 | Sanborn et al. |
| 2007/0284361 A1 | 12/2007 | Nadjafizadeh et al. |
| 2007/0293786 A1 | 12/2007 | Wekell et al. |
| 2008/0000474 A1 | 1/2008 | Jochle et al. |
| 2008/0015475 A1 | 1/2008 | Lau et al. |
| 2008/0053441 A1 | 3/2008 | Gottlib et al. |
| 2008/0072896 A1 | 3/2008 | Setzer et al. |
| 2008/0072900 A1 | 3/2008 | Kenyon et al. |
| 2008/0072902 A1 | 3/2008 | Setzer et al. |
| 2008/0078390 A1 | 4/2008 | Milne et al. |
| 2008/0078395 A1 | 4/2008 | Ho et al. |
| 2008/0083644 A1 | 4/2008 | Janbakhsh et al. |
| 2008/0092894 A1 | 4/2008 | Nicolazzi et al. |
| 2008/0097234 A1 | 4/2008 | Nicolazzi et al. |
| 2008/0127976 A1 | 6/2008 | Acker et al. |
| 2008/0142013 A1 | 6/2008 | Hallett et al. |
| 2008/0190421 A1 | 8/2008 | Zitting |
| 2008/0223316 A1 | 9/2008 | Banta et al. |
| 2009/0000615 A1 | 1/2009 | Pohlmann et al. |
| 2009/0165795 A1 | 7/2009 | Nadjafizadeh et al. |
| 2009/0171176 A1 | 7/2009 | Andersohn |
| 2009/0194101 A1 | 8/2009 | Kenyon et al. |
| 2009/0194112 A1 | 8/2009 | Gunaratnam et al. |
| 2009/0205661 A1 | 8/2009 | Stephenson et al. |
| 2009/0205663 A1 | 8/2009 | Vandine et al. |
| 2009/0241952 A1 | 10/2009 | Nicolazzi et al. |
| 2009/0241953 A1 | 10/2009 | Vandine et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0241965 A1 | 10/2009 | Sather et al. |
| 2009/0247849 A1 | 10/2009 | McCutcheon et al. |
| 2009/0247853 A1 | 10/2009 | Debreczeny |
| 2009/0247891 A1 | 10/2009 | Wood |
| 2009/0266359 A1 | 10/2009 | Flint |
| 2009/0301482 A1 | 12/2009 | Burton et al. |
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |
| 2009/0314294 A1 | 12/2009 | Chalvignac |
| 2010/0011307 A1 | 1/2010 | Desfossez et al. |
| 2010/0024820 A1 | 2/2010 | Bourdon |
| 2010/0051026 A1 | 3/2010 | Graboi |
| 2010/0051029 A1 | 3/2010 | Jafari et al. |
| 2010/0063368 A1 | 3/2010 | Leuthardt et al. |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0078017 A1 | 4/2010 | Andrieux et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0101573 A1 | 4/2010 | Foley et al. |
| 2010/0108070 A1 | 5/2010 | Kwok |
| 2010/0126506 A1 | 5/2010 | Kepler et al. |
| 2010/0132708 A1 | 6/2010 | Martin et al. |
| 2010/0139660 A1 | 6/2010 | Adahan |
| 2010/0147302 A1 | 6/2010 | Selvarajan et al. |
| 2010/0147303 A1 | 6/2010 | Jafari et al. |
| 2010/0170509 A1 | 7/2010 | Moody et al. |
| 2010/0170512 A1 | 7/2010 | Kuypers et al. |
| 2010/0186744 A1 | 7/2010 | Andrieux |
| 2010/0192094 A1 | 7/2010 | Jeha et al. |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0229862 A1 | 9/2010 | Boussignac |
| 2010/0229865 A1 | 9/2010 | Boussignac |
| 2010/0236555 A1 | 9/2010 | Jafari et al. |
| 2010/0242961 A1 | 9/2010 | Mougel et al. |
| 2010/0249549 A1 | 9/2010 | Baker, Jr. et al. |
| 2010/0249630 A1 | 9/2010 | Droitcour et al. |

(56) References Cited

U.S. PATENT DOCUMENTS

| | | |
|---|---|---|
| 2010/0252037 A1 | 10/2010 | Wondka et al. |
| 2010/0252040 A1 | 10/2010 | Kapust et al. |
| 2010/0252041 A1 | 10/2010 | Kapust et al. |
| 2010/0252042 A1 | 10/2010 | Kapust et al. |
| 2010/0269821 A1 | 10/2010 | Larsson et al. |
| 2010/0282259 A1 | 11/2010 | Figueiredo et al. |
| 2010/0288283 A1 | 11/2010 | Campbell et al. |
| 2010/0300446 A1 | 12/2010 | Nicolazzi et al. |
| 2010/0319689 A1 | 12/2010 | Kwok et al. |
| 2011/0005520 A1 | 1/2011 | Doshi et al. |
| 2011/0011400 A1 | 1/2011 | Gentner et al. |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1 | 2/2011 | Thiessen |
| 2011/0041849 A1 | 2/2011 | Chen et al. |
| 2011/0041850 A1 | 2/2011 | Vandine et al. |
| 2011/0073112 A1 | 3/2011 | DiBlasi et al. |
| 2011/0079222 A1 | 4/2011 | DiBlasi et al. |
| 2011/0098592 A1 | 4/2011 | Colman et al. |
| 2011/0120472 A1 | 5/2011 | Lee et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132360 A1 | 6/2011 | Feldhahn et al. |
| 2011/0132361 A1 | 6/2011 | Sanchez |
| 2011/0132362 A1 | 6/2011 | Sanchez |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0154241 A1 | 6/2011 | Skidmore et al. |
| 2011/0175728 A1 | 7/2011 | Baker, Jr. |
| 2011/0196251 A1 | 8/2011 | Jourdain et al. |
| 2011/0197892 A1 | 8/2011 | Koledin |
| 2011/0203589 A1 | 8/2011 | Fenton |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0230780 A1 | 9/2011 | Sanborn et al. |
| 2011/0249006 A1 | 10/2011 | Wallace et al. |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |
| 2011/0265024 A1 | 10/2011 | Leone et al. |
| 2011/0271960 A1 | 11/2011 | Milne et al. |
| 2011/0273299 A1 | 11/2011 | Milne et al. |
| 2012/0000467 A1 | 1/2012 | Milne et al. |
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0012107 A1 | 1/2012 | Howe, Jr. et al. |
| 2012/0029317 A1 | 2/2012 | Doyle et al. |
| 2012/0030611 A1 | 2/2012 | Skidmore |
| 2012/0048276 A1 | 3/2012 | Gunaratnam et al. |
| 2012/0060841 A1 | 3/2012 | Crawford, Jr. et al. |
| 2012/0071729 A1 | 3/2012 | Doyle et al. |
| 2012/0090611 A1 | 4/2012 | Graboi et al. |
| 2012/0096381 A1 | 4/2012 | Milne et al. |
| 2012/0132211 A1 | 5/2012 | Halperin et al. |
| 2012/0133519 A1 | 5/2012 | Milne et al. |
| 2012/0136222 A1 | 5/2012 | Doyle et al. |
| 2012/0137249 A1 | 5/2012 | Milne et al. |
| 2012/0137250 A1 | 5/2012 | Milne et al. |
| 2012/0145155 A1 | 6/2012 | Peake et al. |
| 2012/0152255 A1 | 6/2012 | Barlow et al. |
| 2012/0167885 A1 | 7/2012 | Masic et al. |
| 2012/0185792 A1 | 7/2012 | Kimm et al. |
| 2012/0192870 A1 | 8/2012 | Dugan et al. |
| 2012/0197578 A1 | 8/2012 | Vig et al. |
| 2012/0197580 A1 | 8/2012 | Vij et al. |
| 2012/0211008 A1 | 8/2012 | Perine et al. |
| 2012/0215126 A1 | 8/2012 | Gavriely et al. |
| 2012/0216809 A1 | 8/2012 | Milne et al. |
| 2012/0216810 A1 | 8/2012 | Jafari et al. |
| 2012/0216811 A1 | 8/2012 | Kimm et al. |
| 2012/0226444 A1 | 9/2012 | Milne et al. |
| 2012/0247471 A1 | 10/2012 | Masic et al. |
| 2012/0272960 A1 | 11/2012 | Milne |
| 2012/0272961 A1 | 11/2012 | Masic et al. |
| 2012/0272962 A1 | 11/2012 | Doyle et al. |
| 2012/0277616 A1 | 11/2012 | Sanborn et al. |
| 2012/0279501 A1 | 11/2012 | Wallace et al. |
| 2012/0304995 A1 | 12/2012 | Kauc |
| 2012/0304997 A1 | 12/2012 | Jafari et al. |
| 2013/0000644 A1 | 1/2013 | Thiessen |
| 2013/0006133 A1 | 1/2013 | Doyle et al. |
| 2013/0006134 A1 | 1/2013 | Doyle et al. |
| 2013/0008443 A1 | 1/2013 | Thiessen |
| 2013/0025596 A1 | 1/2013 | Jafari et al. |
| 2013/0025597 A1 | 1/2013 | Doyle et al. |
| 2013/0032151 A1 | 2/2013 | Adahan |
| 2013/0042869 A1 | 2/2013 | Andrieux et al. |
| 2013/0047983 A1 | 2/2013 | Andrieux et al. |
| 2013/0047989 A1 | 2/2013 | Vandine et al. |
| 2013/0053717 A1 | 2/2013 | Vandine et al. |
| 2013/0074844 A1 | 3/2013 | Kimm et al. |
| 2013/0081536 A1 | 4/2013 | Crawford, Jr. et al. |
| 2013/0104896 A1 | 5/2013 | Kimm et al. |
| 2013/0146055 A1 | 6/2013 | Jafari et al. |
| 2013/0167842 A1 | 7/2013 | Jafari et al. |
| 2013/0167843 A1 | 7/2013 | Kimm et al. |
| 2013/0192599 A1 | 8/2013 | Nakai et al. |
| 2013/0220324 A1 | 8/2013 | Jafari et al. |
| 2013/0255682 A1 | 10/2013 | Jafari et al. |
| 2013/0255685 A1 | 10/2013 | Jafari et al. |
| 2013/0284172 A1 | 10/2013 | Doyle et al. |
| 2013/0284177 A1 | 10/2013 | Li et al. |
| 2014/0000606 A1 | 1/2014 | Doyle et al. |
| 2014/0012150 A1 | 1/2014 | Milne et al. |
| 2014/0034054 A1 | 2/2014 | Angelico et al. |
| 2014/0123979 A1 | 5/2014 | Doyle et al. |

OTHER PUBLICATIONS

7200 Series Ventilator, Options, and Accessories: Operator's Manual. Nellcor Puritan Bennett, Part No. 22300 A, Sep. 1990, pp. 1-196.
7200 Ventilatory System: Addendum/Errata. Nellcor Puritan Bennett, Part No. 4-023576-00, Rev. A, Apr. 1998, pp. 1-32.
800 Operator's and Technical Reference Manual. Series Ventilator System, Nellcor Puritan Bennett, Part No. 4-070088-00, Rev. L, Aug. 2010, pp. 1-476.
840 Operator's and Technical Reference Manual. Ventilator System, Nellcor Puritan Bennett, Part No. 4-075609-00, Rev. G, Oct. 2006, pp. 1-424.

* cited by examiner

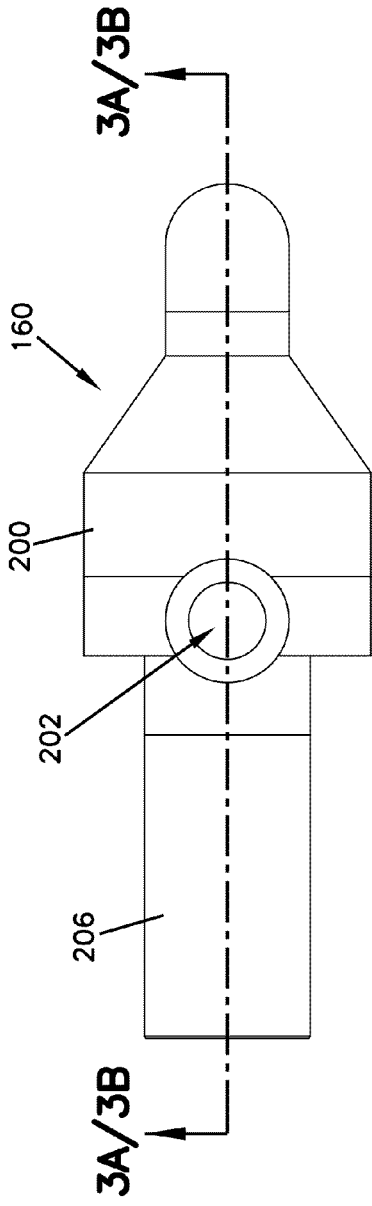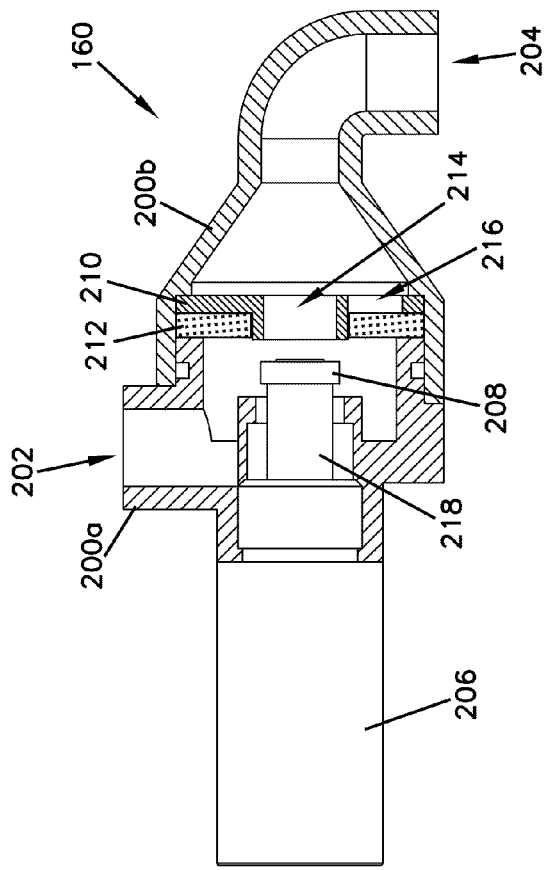
FIG. 2C
FIG. 3A

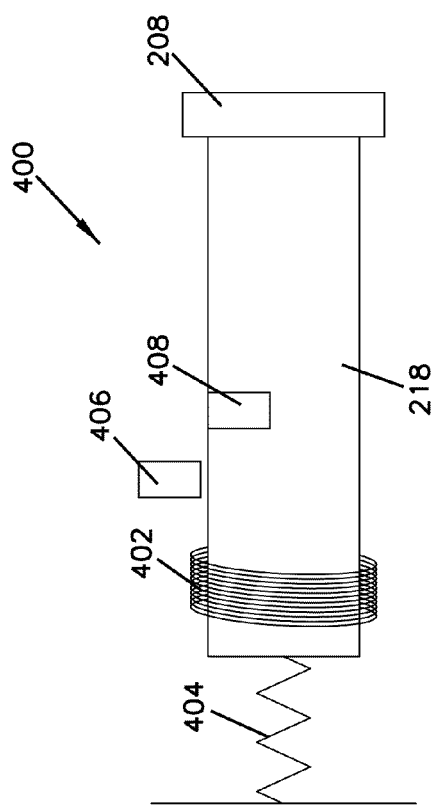
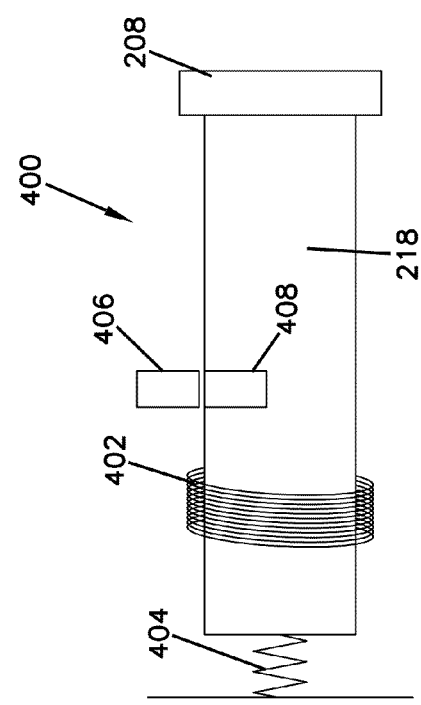
FIG. 4A
FIG. 4B

VENTILATOR PRESSURE OSCILLATION FILTER

GOVERNMENT LICENSE RIGHTS STATEMENT

This invention was made with government support under grant number HHSO100201000060C awarded by the Office of the Assistant Secretary for Preparedness and Response (ASPR), the Biomedical Advanced Research and Development Authority (BARDA). The government has certain rights in the invention.

INTRODUCTION

Medical ventilator systems have long been used to provide ventilatory and supplemental oxygen support to patients. Although medical ventilators can be used across a wide range of patients, from adult to pediatric to neonatal, certain considerations are required for each particular patient group. Neonates, specifically, have particular flow requirements that often require modification to the ventilator output to properly ventilate the neonate patient.

This disclosure describes filters that optimize flow requirements for neonatal patients.

In part, this disclosure describes a ventilation air pressure oscillation mitigation device for a ventilator, the oscillation mitigation device including: a housing defining an inlet and an outlet; a valve seat defining a primary opening and a plurality of secondary openings; a valve body selectively positionable in a first position and a second position, wherein when the valve body is in the first position, substantially all of a first flow of ventilation air from the inlet to the outlet passes through the primary opening, and wherein when the valve body is in the second position, all of a second flow of ventilation air from the inlet to the outlet passes through the plurality of secondary openings; and an actuator for controlling a position of the valve body.

It is to be understood that both the foregoing general description and the following detailed description are exemplary and explanatory and are intended to provide further explanation of the technology as claimed.

BRIEF DESCRIPTION OF THE DRAWINGS

The following drawing figures, which form a part of this application, are illustrative of embodiments of systems and methods described below and are not meant to limit the scope of the technology in any manner, which scope shall be based on the claims.

FIGS. 2A-2C depict perspective, exploded perspective, and top views, respectively, of a pressure oscillation filter to be used in a ventilator.

FIG. 3A depicts the pressure oscillation filter of FIGS. 2A-2C in a flow-through mode.

FIGS. 4A and 4B depict a valve operator.

DETAILED DESCRIPTION

Although the techniques introduced above and discussed in detail below may be implemented for a variety of medical devices, the present disclosure will discuss the implementation of these techniques for use in a mechanical ventilator system. The reader will understand that the technology described in the context of a ventilator system could be adapted for use with other therapeutic equipment providing oscillatory pressure controlled delivery of gas flow to a patient.

This disclosure describes systems and methods for configuring a ventilator to determine oscillatory pressure controlled delivery of gas flow to a patient. According to embodiments, an average target pressure may be determined and an oscillating waveform may be imposed substantially about the average target pressure value. Upper and lower oscillatory bounds may be defined, as well as a time duration for a single oscillation. Oscillatory waveforms may dynamically adapt to changes in patient parameters on a breath-by-breath basis to provide optimum gas flow to a patient.

Figure 1A:
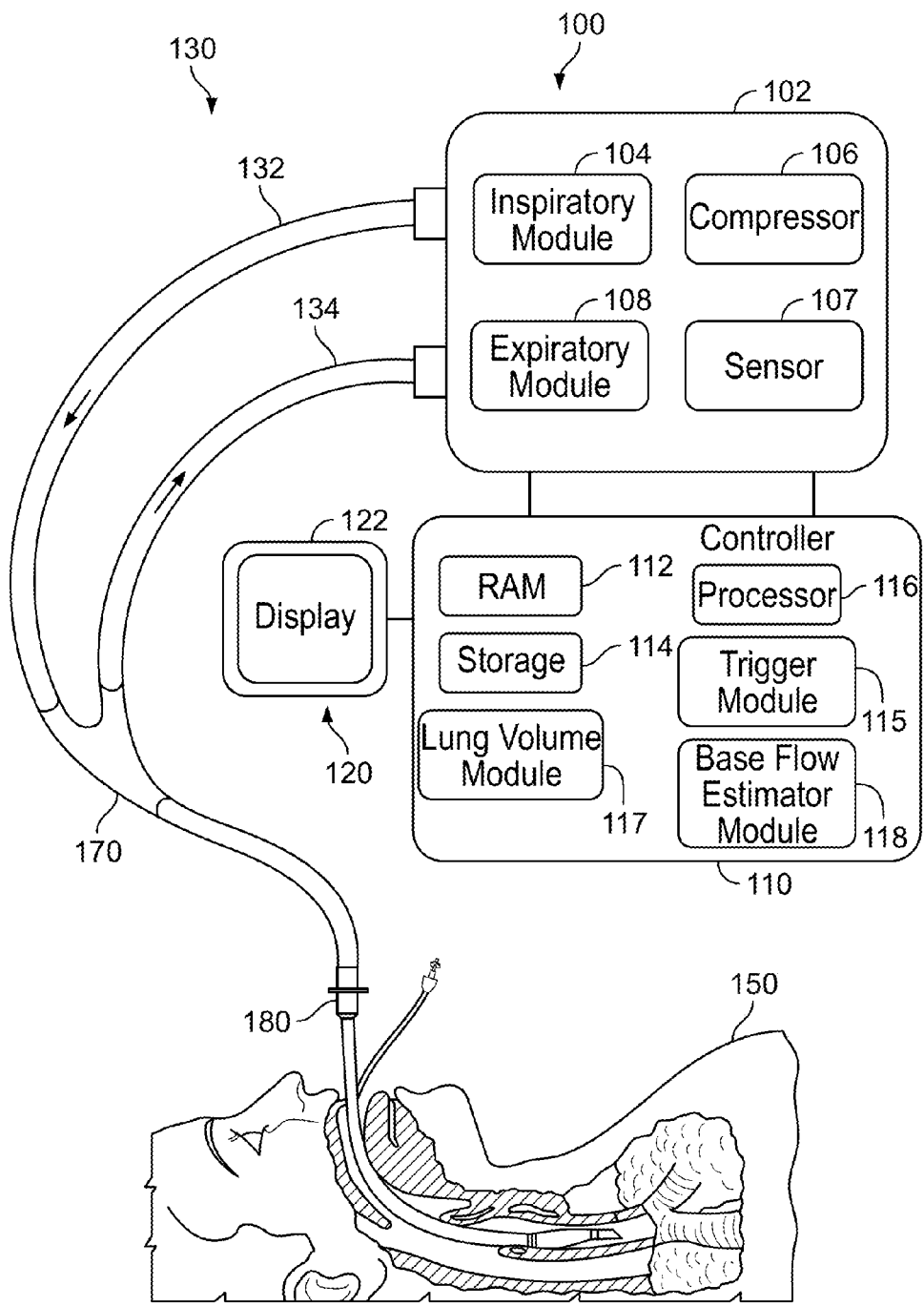
FIGS. 1A and 1B depict a ventilator.
Figure 1B:
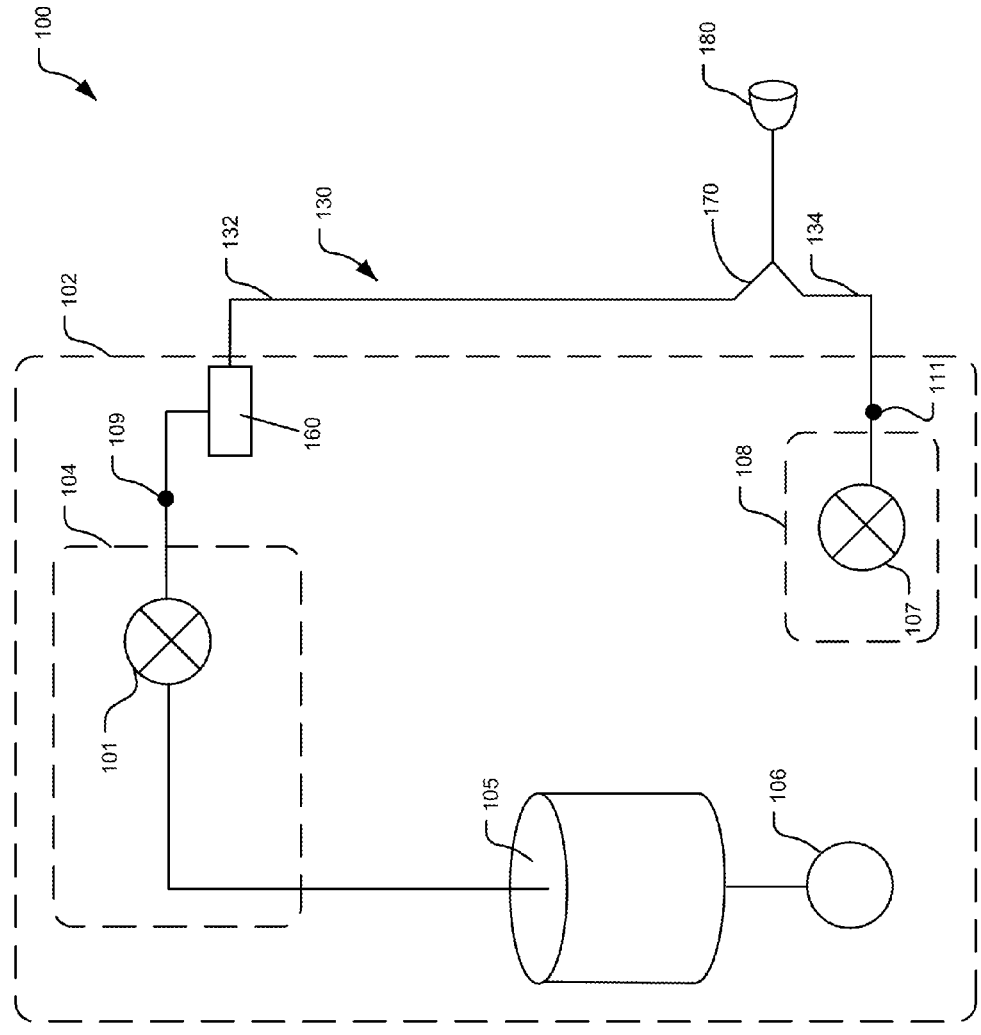

FIGS. 1A and 1B are diagrams illustrating two embodiments of an exemplary ventilator 100. It should be noted, however, that the components described below in only a single embodiment may also be included in the other embodiment (for example, an accumulator is depicted in FIG. 1B, but could also be included in the ventilator of FIG. 1A). The exemplary ventilator 100 illustrated in FIG. 1A is connected to a human patient 150. Ventilator 100 includes a pneumatic system 102 (also referred to as a pressure generating system 102) for circulating breathing gases to and from patient 150 via the ventilation tubing system 130, which couples the patient 150 to the pneumatic system 102 via an invasive (e.g., endotracheal tube, as shown) or a non-invasive (e.g., nasal mask) patient interface 180.

Ventilation tubing system 130 (or patient circuit 130) may be a two-limb (shown) or a one-limb circuit for carrying gases to and from the patient 150. In a two-limb embodiment, a fitting, typically referred to as a "wye-fitting" 170, may be provided to couple the patient interface 180 (shown as an endotracheal tube in FIG. 1A and as a nasal mask in FIG. 1B) to an inspiratory limb 132 and an expiratory limb 134 of the ventilation tubing system 130.

Pneumatic system 102 may be configured in a variety of ways. In FIG. 1A, pneumatic system 102 includes an expiratory module 108 coupled with the expiratory limb 134 and an inspiratory module 104 coupled with the inspiratory limb 132. FIG. 1B depicts a compressor 106, an accumulator 105, and may include other source(s) of pressurized gases (e.g., air, oxygen, and/or helium) coupled with inspiratory module 104 and the expiratory module 108 to provide a gas source for ventilatory support via inspiratory limb 132.

The inspiratory module 104 is configured to deliver gases to the patient 150 and/or through the inspiratory limb 132 according to prescribed ventilatory settings. The inspiratory module 104 is associated with and/or controls an inspiratory valve 101 for controlling gas delivery to the patient 150 and/or gas delivery through the inspiratory limb 132. In some embodiments, inspiratory module 104 is configured to provide ventilation according to various ventilator modes, such as mandatory and assist modes.

The expiratory module 108 is configured to release gases from the patient's lungs according to prescribed ventilatory settings. The expiratory module 108 is associated with and/or controls an expiratory valve 107 for releasing gases from the patient 150. Further, the expiratory module 108 and/or the inspiratory module 104 may instruct the pressure generating system 102 and/or the inspiratory module 104 to deliver a base flow during exhalation. In an alternative embodiment, the pressure generating system 102 may instruct the inspiratory module 104 to deliver a base flow during exhalation.

The ventilator 100 may also include one or more sensors 124 communicatively coupled to ventilator 100. The sensors 124 may be located in the pneumatic system 102, ventilation tubing system 130, and/or on the patient 150. The embodiment of FIG. 1A illustrates a sensor 124 in pneumatic system 102.

Sensors 124 may communicate with various components of ventilator 100, e.g., pneumatic system 102, other sensors 124, expiratory module 108, inspiratory module 104, processor 116, controller 110, trigger module 115, lung volume module 117, base flow estimator module 118, and any other suitable components and/or modules. In one embodiment, sensors 124 generate output and send this output to pneumatic system 102, other sensors 124, expiratory module 108, inspiratory module 104, processor 116, controller 110 trigger module 115, lung volume module 117, base flow estimator module 118, and any other suitable components and/or modules.

Sensors 124 may employ any suitable sensory or derivative technique for monitoring one or more patient parameters or ventilator parameters associated with the ventilation of a patient 150. Sensors 124 may detect changes in patient parameters indicative of patient inspiratory or expiratory triggering, for example. Sensors 124 may be placed in any suitable location, e.g., within the ventilatory circuitry or other devices communicatively coupled to the ventilator 100. Further, sensors 124 may be placed in any suitable internal location, such as, within the ventilatory circuitry or within components or modules of ventilator 100. For example, sensors 124 may be coupled to the inspiratory and/or expiratory modules 104, 108 for detecting changes in, for example, circuit pressure and/or flow. In other examples, sensors 124 may be affixed to the ventilatory tubing or may be embedded in the tubing itself. According to some embodiments, sensors 124 may be provided at or near the lungs (or diaphragm) for detecting a pressure in the lungs. Additionally or alternatively, sensors 124 may be affixed or embedded in or near wye-fitting 170 and/or patient interface 180. Any sensory device useful for monitoring changes in measurable parameters during ventilatory treatment may be employed in accordance with embodiments described herein.

For example, in some embodiments, the one or more sensors 124 of the ventilator 100 include an inspiratory flow sensor 109 and an expiratory flow sensor 111 as illustrated in FIG. 1B. In one embodiment, the inspiratory flow sensor 109 is located in the inspiratory limb 132 and is controlled by the inspiratory module 104. However, the inspiratory flow sensor 109 may be located in any suitable position for monitoring inspiratory flow and may be monitored by any suitable ventilator component, such as a pressure generating system 102. In one embodiment, the expiratory flow sensor 111 is located in the expiratory limb 134 and is monitored by the expiratory module 108. However, the expiratory flow sensor 111 may be located in any suitable position for monitoring expiratory flow and may be monitored by any suitable ventilator component, such as a pressure generating system 102.

As should be appreciated, ventilatory parameters are highly interrelated and, according to embodiments, may be either directly or indirectly monitored. That is, parameters may be directly monitored by one or more sensors 124, as described above, or may be indirectly monitored or estimated by derivation according to any known relationships, assumptions, or other factors.

The pneumatic system 102 may include a variety of other components, including mixing modules, valves, tubing, accumulators 105, filters, etc. One such component is a pressure oscillation filter 160 that may be located on the inspiratory limb 132. The pressure oscillation filter 160 may be manually actuated or may be controlled by the controller 110, as described below. Controller 110 is operatively coupled with pneumatic system 102, signal measurement and acquisition systems, and an operator interface 120 that may enable an operator to interact with the ventilator 100 (e.g., change ventilator settings, select operational modes, view monitored parameters, etc.).

In one embodiment, the operator interface 120 of the ventilator 100 includes a display 122 communicatively coupled to ventilator 100. Display 122 provides various input screens, for receiving clinician input, and various display screens, for presenting useful information to the clinician. In one embodiment, the display 122 is configured to include a graphical user interface (GUI). The GUI may be an interactive display, e.g., a touch-sensitive screen or otherwise, and may provide various windows and elements for receiving input and interface command operations. Alternatively, other suitable means of communication with the ventilator 100 may be provided, for instance by a wheel, keyboard, mouse, or other suitable interactive device. Thus, operator interface 120 may accept commands and input through display 122.

Display 122 may also provide useful information in the form of various ventilatory data regarding the physical condition of a patient 150. The useful information may be derived by the ventilator 100, based on data collected by a processor 116, and the useful information may be displayed to the clinician in the form of graphs, wave representations, pie graphs, text, or other suitable forms of graphic display. For example, patient data may be displayed on the GUI and/or display 122. Additionally or alternatively, patient data may be communicated to a remote monitoring system coupled via any suitable means to the ventilator 100. In some embodiments, the display 122 may illustrate a WDLV, a net negative change in lung volume, an estimated base flow, an exhalation flow, a restricted period, a trigger threshold, a sampling period for the WDLV and/or any other information known, received, or stored by the ventilator 100.

In some embodiments, controller 110 includes memory 112, one or more processors 116, storage 114, and/or other components of the type commonly found in command and control computing devices. Controller 110 may further include a trigger module 115, lung volume module 117, and base flow estimator module 118, as illustrated in FIG. 1A. In alternative embodiments, the trigger module 115, lung volume module 117, and base flow estimator module 118 are located in other components of the ventilator 100, such as in the pressure generating system 102 (also known as the pneumatic system 102).

The memory 112 includes non-transitory, computer-readable storage media that stores software that is executed by the processor 116 and which controls the operation of the ventilator 100. In an embodiment, the memory 112 includes one or more solid-state storage devices such as flash memory chips. In an alternative embodiment, the memory 112 may be mass storage connected to the processor 116 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 116. That is, computer-readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

In one embodiment, the ventilator may be a modified version of the HT70 Plus Ventilator manufactured by Newport Medical Instruments, Inc. of Costa Mesa, Calif. The HT70 Plus is intended to provide continuous or intermittent positive pressure ventilatory support to patients requiring respiratory medical care in hospital, sub-acute, emergency room, home care, transport and emergency response applications. The ventilator technology described herein addresses new indications for use of any ventilator for neonate patients with pressure release ventilation. The HT70 Plus Ventilator, as well as other ventilators, utilize a micro-piston pump compressor to deliver pressurized air to the patient. One advantage of the micro-piston pump technology compared to other types of compressors is the power efficiency resulting in extended operation between battery charges or replacement. One micro-piston pump and motor system is described in U.S. Pat. No. 7,654,802, the disclosure of which is hereby incorporated by reference herein in its entirety. In such a system, motor electronics drive a brushless motor connected to a linkage system to create a reciprocating motion. This motion drives dual pistons in two chambers, thus creating four pressurized cavities. The cyclic displacement of the pistons creates flow through the one-way inlet and outlet valves in each cavity. One challenge of a reciprocating pump is the superposition of the pressure pulsations or oscillations from each individual cavity. One measure to address this effect is an internal silicone diaphragm positioned on the pump outlet. The diaphragm expands and contracts to control pressure disturbances. Another method is the relative position or phase of each of the piston during the stroke. However, these technologies may not be sufficient to adequately control pressure oscillations for neonate patients.

Further mitigation of the pressure oscillations is therefore desirable to enhance ventilator performance especially for low flow applications including small breaths for neonate size patients. In brief, the detection sensitivity of patient inspiratory effort is dependent on the amount of noise or pressure oscillations delivered by the pump. Technologies that address this issue are described in more detail below.

Figure 2A:
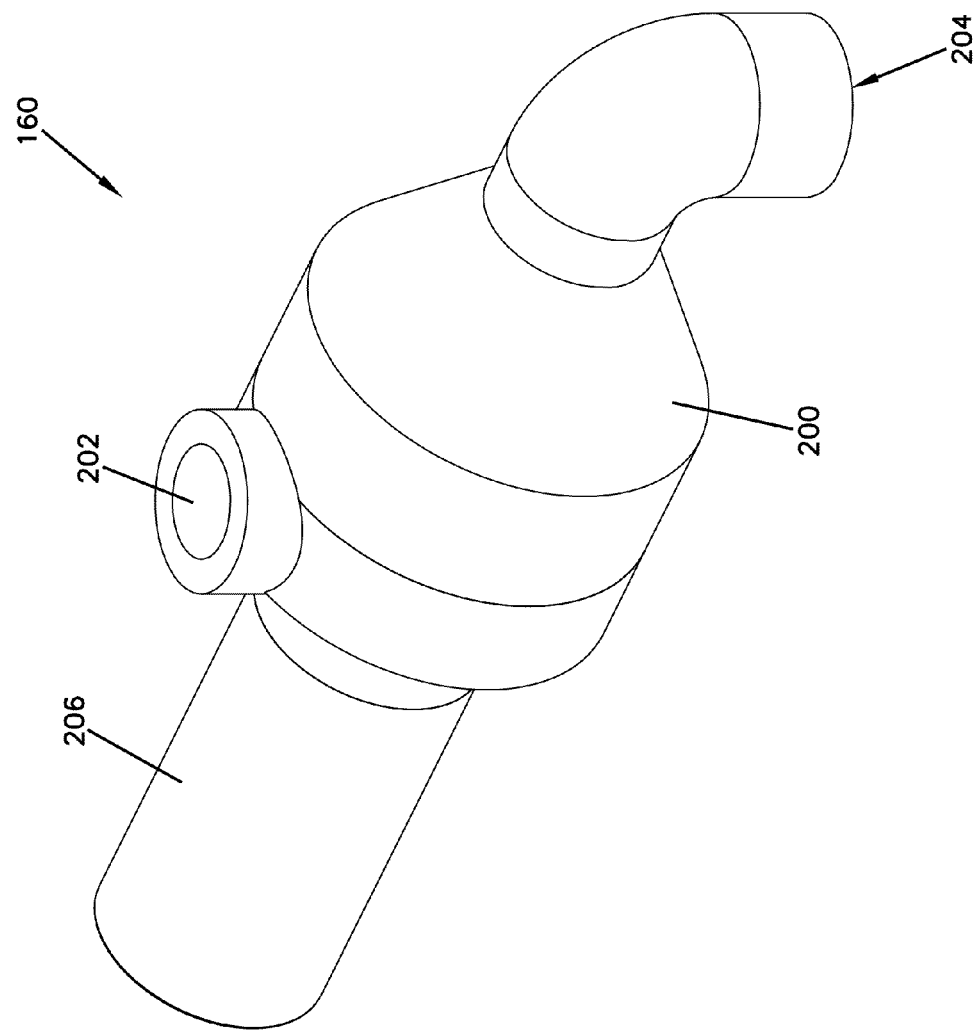
Figure 2B:
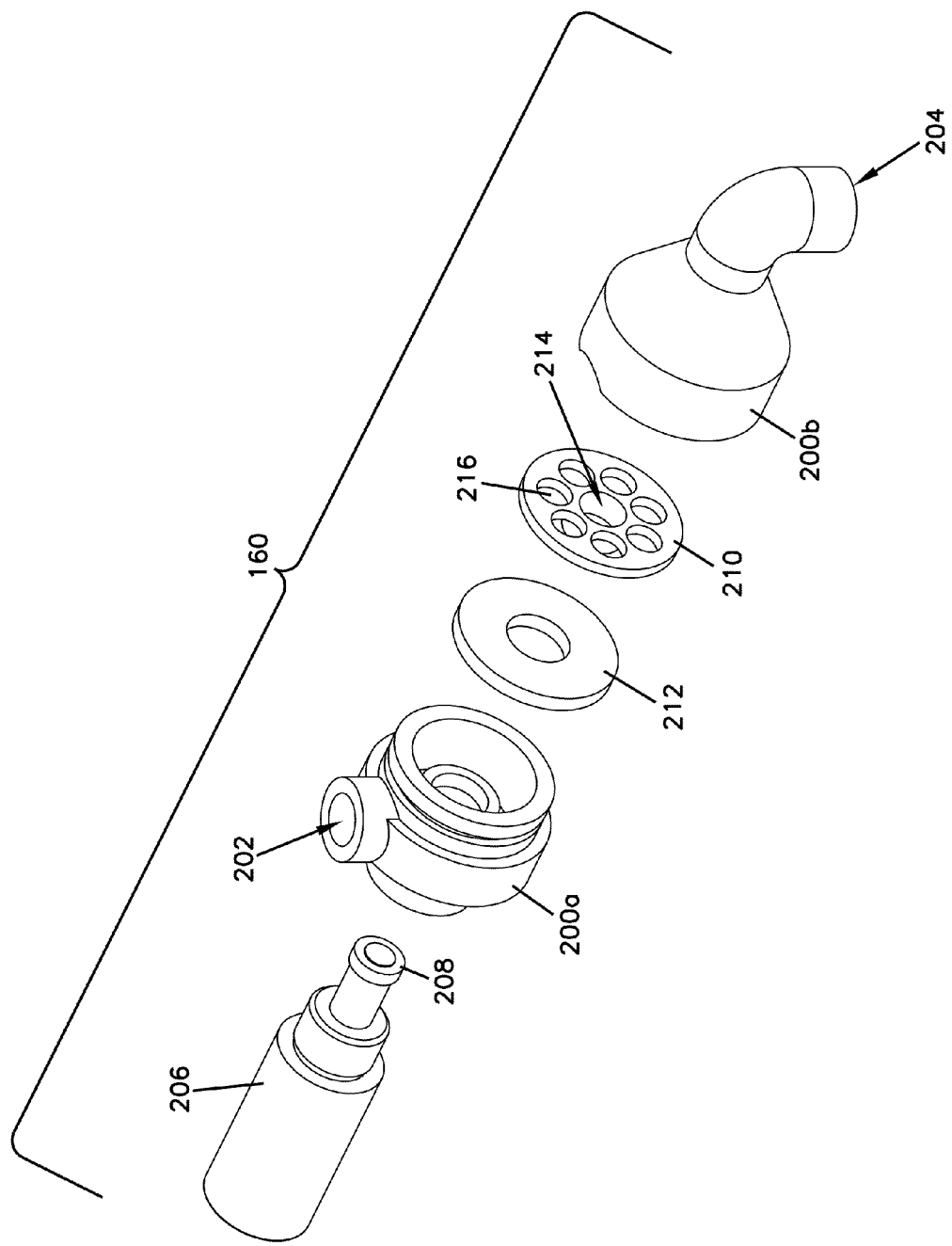
Figure 3B:
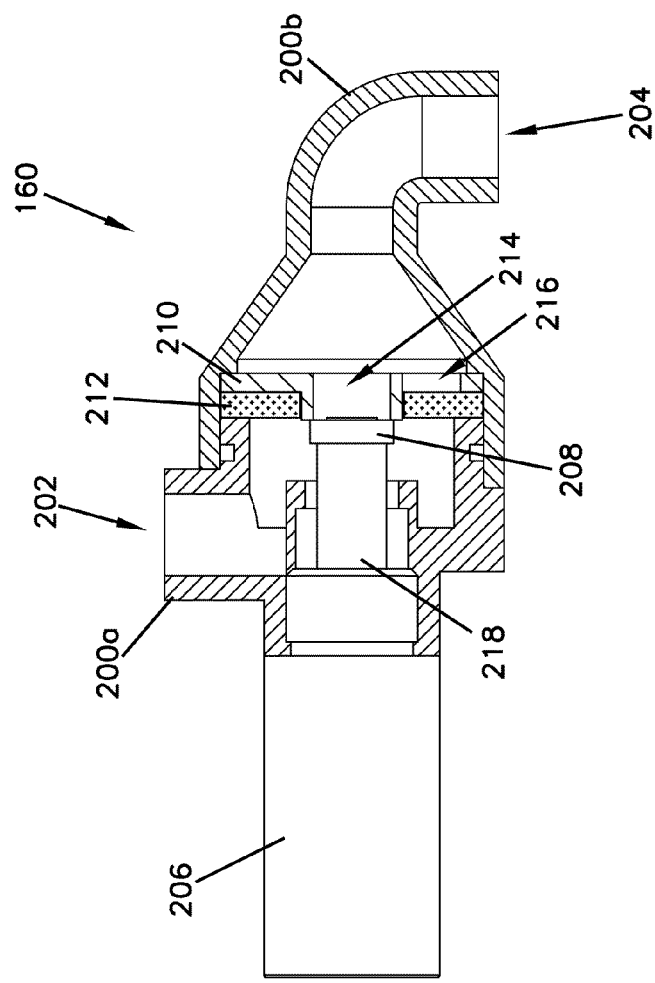
FIG. 3B depicts the pressure oscillation filter of FIG. 3A in a bypass mode.

FIGS. 2A-2C depict various views of the ventilation air pressure oscillation mitigation device 160 originally described in FIG. 1B. The device 160 includes a housing 200 that defines a ventilation air inlet 202 and a ventilation air outlet 204. The relative positions of the inlet 202 and outlet 204 may vary depending on actual implementation and further design considerations. A solenoid 206 is secured to a portion of the housing 200 and actuates a valve body 208. Two portions 200a, 200b of the housing, when joined together, form an internal chamber (FIGS. 3A-3B). Located within the internal chamber are a valve seat 210 and a filter media 212. The valve seat 210 defines a primary opening 214 that in the depicted embodiment is centrally located. The location of the primary opening 214 is not critical, provided it is aligned with the valve body 208. A plurality of secondary openings 216 surround the primary opening 214. The filter media 212 may be a porous polyethylene having a porosity of about 90 to about 100 microns. The filter media 212 includes a plurality of small passages such as pores or a webbing in a screen to optimize filtering and maintaining the required pressure differential and flow rate. Other types and configurations of filter media are contemplated. For example, a filter of plastic or fine metal mesh may be utilized.

FIG. 3A depicts the ventilation air pressure oscillation mitigation device 160 in an "adult" or "unrestricted flow" mode. When the ventilator is delivering ventilation air to an adult and the device 160 is in the unrestricted flow mode, the flow is relatively high and the resistance of the gas flow path must be low to meet the flow specifications. The maximum flow of the pump is limited by the pump discharge pressure which is affected by the internal gas path resistance and the circuit pressure. To keep the flow high, the valve body 208 is in a first position and exposes the primary opening 214 for flow. The primary opening 214 size and distance to valve body 208 is balanced to maximize flow. In one embodiment, the primary opening 214 has a diameter of about $5/16$" and the distance between the valve body 208 and the primary opening 214 is about $1/8$". It has been discovered that other embodiments of the device 160 having other primary opening 214 diameters may improve ventilator (especially compressor) performance. For example, an increase in the diameter of about $1/8$" (that is, from about 5/16" to about $7/16$") increases pump efficiency by about 10%.

FIG. 3B depicts the ventilation air pressure oscillation mitigation device 160 in a neonate" or "restricted flow" mode. For neonate patients, the maximum flow is substantially less than adult flow. The difference in the flow requirements provides an opportunity to increase the resistance in the gas flow path and enable the use of the mitigation device 160 to filter the oscillations. In the restricted flow mode, the valve body 208 is in a second position and blocks the primary opening 214. A valve body extension 218 may be an elastic material to provide high cycles without failure. Minor leakage between the valve body 208 and the primary opening 214 will not significantly affect performance. When in this position, air flow is diverted through the secondary openings 216, via the filter media 212. The secondary openings 214 are depicted in the figures as surrounding the primary opening, both other configurations are also contemplated. For example, a valve body 208 may have any number of openings of any shape or dimension. In certain embodiments, the valve body 208 may be a lattice, screen, cross member, or other structure that simply provides support to the filter media 212 without obstructing flow therethrough. In certain embodiments, the filter media need not be used. Instead, the valve body may include a larger number of holes having smaller diameters (e.g., about 100-120 holes of about a 0.020" diameter) to provide a similar function to the porous filter media.

Figure 5A:
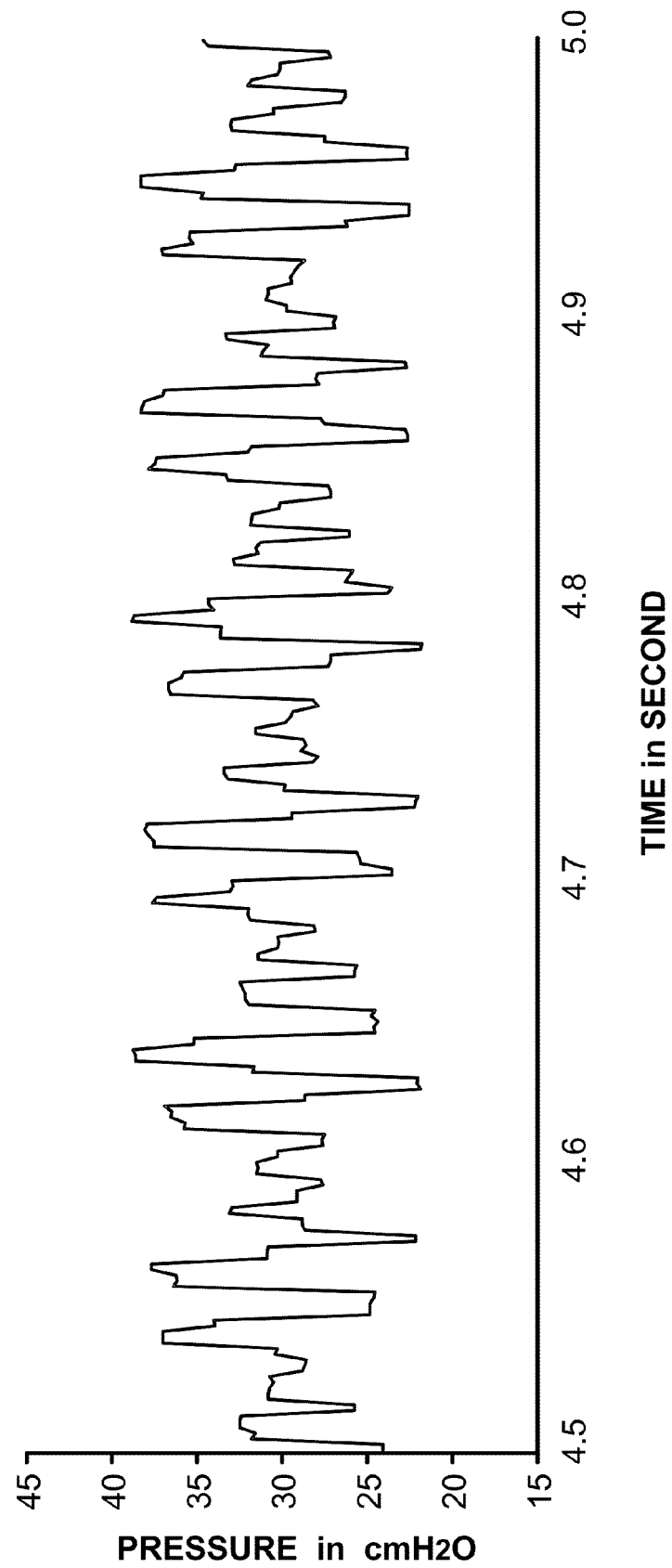
FIG. 5A depicts a pressure waveform for a baseline ventilator with a pressure oscillation filter in the flow-through mode.
Figure 5B:
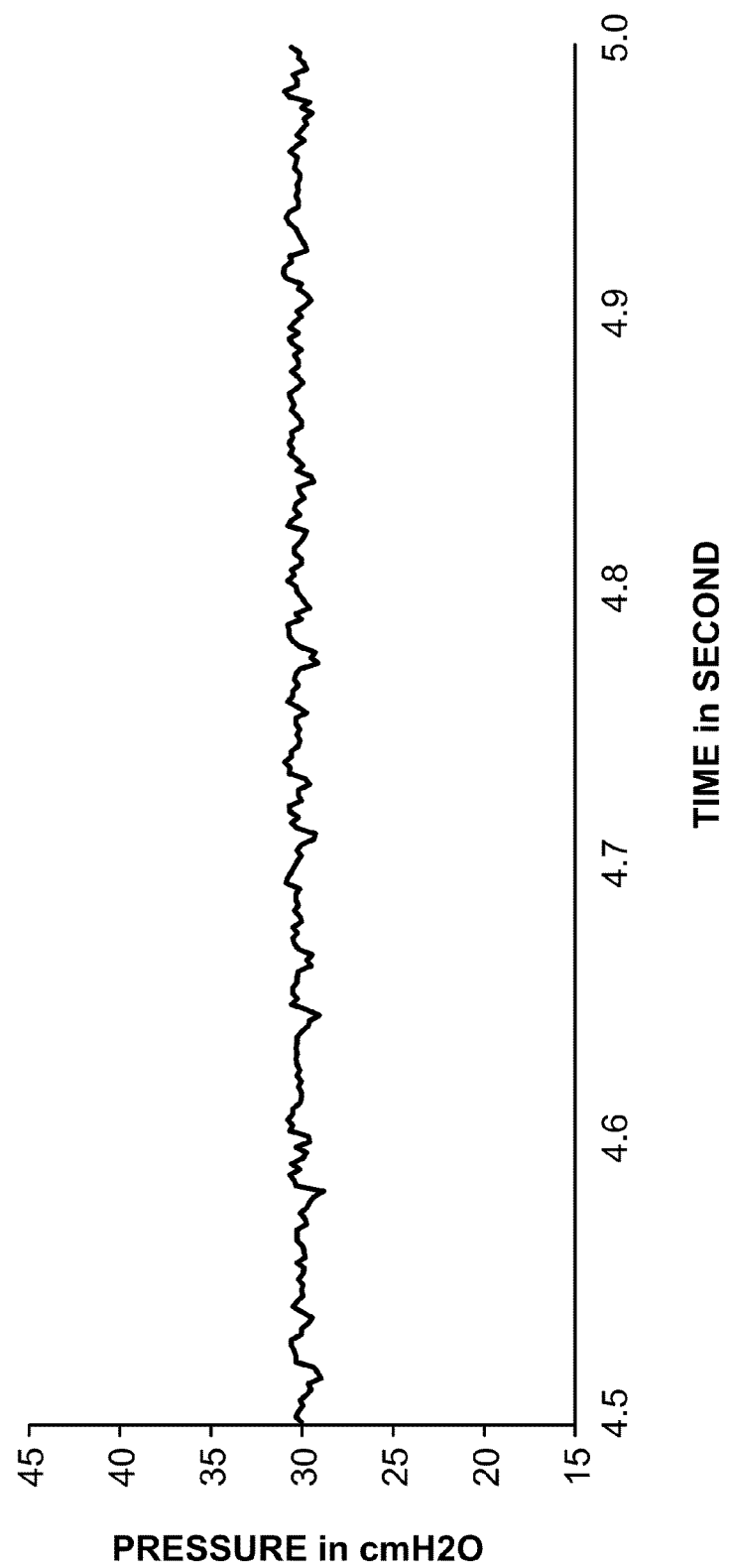
FIG. 5B depicts a pressure waveform for a baseline ventilator with a pressure oscillation filter in the bypass mode.

FIGS. 4A and 4B depict a valve operator 400. The valve operator 400 includes a solenoid coil 402 around the valve body extension 218 and two unpowered elements for holding the valve 208 in either the extended position of FIG. 4A or the retracted position of FIG. 4B. A spring 404 biases the valve 208 in the extended position. A magnet 406 engages with a magnetized element 408 to hold the valve in the retracted position. To change position, the polarity of the coil 402 is reversed and power is applied briefly. Depending on the initial position of the valve 208, the valve 208 will be held in place by either the force of the magnets 406/408 or the spring 404. This allows the solenoid coil 402 to be de-energized regardless of the position in which it is located. The solenoid coil 402 uses a constant current mode in the retracted position due to inductance of the coil 402 to maximize reliability. In addition, an inductance sensing circuit provides a capability to sense the position of the valve body extension 218 in either position to provide additional safety protection. FIGS. 5A and 5B depict the pressure waveform of a ventilator that includes a ventilation air pressure oscillation mitigation device, as described herein. As can be seen in FIG. 5B, when the device is in the neonate mode, the pressure oscillations are significantly decreased. In the neonate mode, the air pressure oscillation mitigation device is sized to function desirably for flow rates of about 7 lpm to about 30 lpm.

Those skilled in the art will recognize that the methods and systems of the present disclosure may be implemented in many manners and as such are not to be limited by the foregoing exemplary embodiments and examples. In other words, functional elements being performed by a single or multiple components, in various combinations of hardware and software or firmware, and individual functions, can be distributed among software applications at either the client or server level or both. In this regard, any number of the features of the different embodiments described herein may be combined into single or multiple embodiments, and alternate embodiments having fewer than or more than all of the features herein described are possible. Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, and those variations and modifications that may be made to the hardware or software firmware components described herein as would be understood by those skilled in the art now and hereafter.

Numerous other changes may be made which will readily suggest themselves to those skilled in the art and which are encompassed in the spirit of the disclosure and as defined in the appended claims. While various embodiments have been described for purposes of this disclosure, various changes and modifications may be made which are well within the scope of the present technology. Numerous other changes may be made which will readily suggest themselves to those skilled in the art and which are encompassed in the spirit of the disclosure and as defined in the claims.

We claim:

1. A ventilation air pressure oscillation mitigation device for a ventilator, the oscillation mitigation device comprising:
    a housing defining an inlet and an outlet;
    a valve seat defining a primary opening and a plurality of secondary openings;
    a valve body selectively positionable in a first position and a second position,
        wherein when the valve body is in the first position, substantially all of a first flow of ventilation air from the inlet to the outlet passes through the primary opening, and
        wherein when the valve body is in the second position, all of a second flow of ventilation air from the inlet to the outlet passes through the plurality of secondary openings; and
    an actuator for controlling a position of the valve body.

2. The ventilation air pressure oscillation mitigation device of claim 1, further comprising a filter media located proximate the plurality of second openings, such that when the valve body is in the second position, the second flow of ventilation air from the inlet to the outlet passes through the plurality of secondary openings and the filter media.

3. The ventilation air pressure oscillation mitigation device of claim 2, wherein the filter media is located upstream of the valve body.

4. The ventilation air pressure oscillation mitigation device of claim 1, wherein the actuator comprises a solenoid.

5. The ventilation air pressure oscillation mitigation device of claim 4, wherein the actuator further comprises a biasing element for holding the valve body in at least one of the first position and the second position.

6. The ventilation air pressure oscillation mitigation device of claim 5, wherein the biasing element comprises a magnet for holding the valve body in the first position.

7. The ventilation air pressure oscillation mitigation device of claim 6, wherein the biasing element further comprises a spring for holding the valve body in the second position.

8. A ventilator comprising an inspiratory limb and the ventilation air pressure oscillation mitigation device of claim 1, located on the inspiratory limb.

* * * * *